United States Patent [19]

Ebach

[11] 4,226,162

[45] Oct. 7, 1980

[54] ATTACHMENT FOR MUSICAL WIND OPERATED INSTRUMENTS

[76] Inventor: Alfred Ebach, Uthmannstrasse 26, 6502 Mainz, Kostheim, Fed. Rep. of Germany

[21] Appl. No.: 898,389

[22] Filed: Apr. 20, 1978

[51] Int. Cl.³ .......................... G10D 9/06; A61B 7/02

[52] U.S. Cl. ........................................ 84/400; 84/453; 84/465; 84/470 R; 181/131; 181/141

[58] Field of Search ............. 84/400, 453, 465, 470 R; 181/131, 137, 141

[56] References Cited

U.S. PATENT DOCUMENTS

| | | | |
|---|---|---|---|
| 2,574,591 | 11/1951 | Rudd | 84/400 |
| 3,392,619 | 7/1968 | Hill | 84/400 |
| 3,555,956 | 1/1971 | Martin | 84/400 |
| 3,760,679 | 9/1973 | Gossick et al. | 84/400 |
| 3,830,334 | 8/1974 | Costa | 181/131 |
| 3,842,706 | 10/1974 | Beversdorf | 84/400 |
| 4,112,809 | 9/1978 | Sjostrand et al. | 84/470 R |

FOREIGN PATENT DOCUMENTS

| | | | |
|---|---|---|---|
| 2709240 | 7/1978 | Fed. Rep. of Germany | 181/131 |

*Primary Examiner*—J. V. Truhe
*Assistant Examiner*—Forester W. Isen
*Attorney, Agent, or Firm*—Webb, Burden, Robinson & Webb

[57] ABSTRACT

A device which consists of a hollow cylindrical member attachable to the end of a musical wind operated instrument. A stethoscope is located inside the hollow body and serves to pick up sounds issuing from the end of the muscial instrument. The hollow member is filled with dissimilar open cell polymeric foams between permeable felt discs.

6 Claims, 1 Drawing Figure

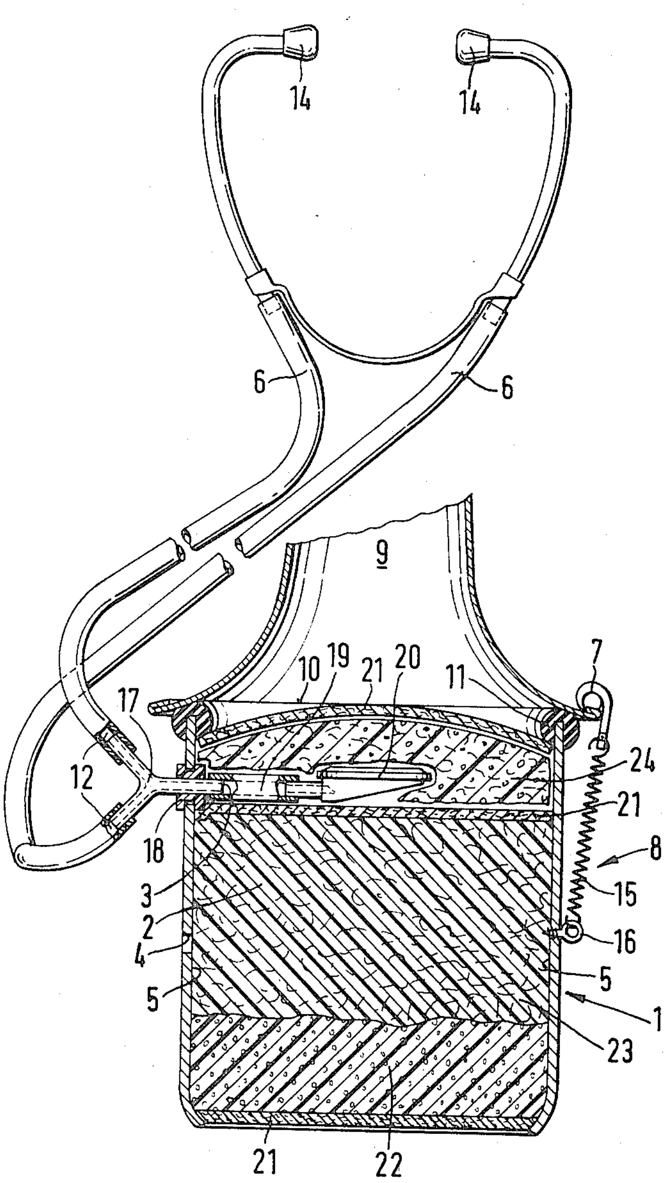
14
14
6
6
9
7
10
19
21
20
11
17
24
12
21
18
8
3
15
2
16
4
5
5
1
23
21
22

ATTACHMENT FOR MUSICAL WIND OPERATED INSTRUMENTS

BACKGROUND

The invention relates to an attachment for musical wind operated instruments.

In numerous types of musical wind operated instruments, such as trumpets, an air stream is periodically interrupted to cause resonance of an air column bounded by a solid body. This resonating air column produces a high intensity sound and as a consequence difficulties are encountered when practicing with such instruments. The instrument player must find a practice room remote from his or her neighbors, for example, the cellar or the loft of a house, so that the neighbors are not disturbed by the sounds caused by practicing. Unfortunately secluded or sound insulated rooms are rarely available and consequently many people who would otherwise be interested in practicing instruments are deterred out of regard for the world around them.

It is an advantage of the present invention to provide a device which enables a wind operated instrument to be practiced without disturbing people in the vicinity of the player.

SUMMARY OF THE INVENTION

According to the present invention there is provided an attachment for a musical wind operated instrument such as a trumpet or the like. The attachment comprises a hollow body and a stethoscope. The hollow body is adapted for releasable attachment to the bell of the wind instrument, such that an aperture of the hollow body is in coaxial relationship with the bell. A membrane of the stethoscope is placed within the hollow body. The membrane is connected with tubes of the stethoscope located at least partially externally of the hollow body.

Preferably the hollow body has a cylindrical shape and has two or more elastically extensible fastening means arranged on the outer surface of the cylinder jacket. The fastening means are provided with hooks for releasable connection to the bell.

The round aperture of the hollow body may have a sealing rim consisting of foam rubber or similar material.

Preferably the upper aperture and the lower aperture of the cylindrical hollow body are each closed by a respective permeable disc, for example felt, and between which there are disposed a third similar disc carrying the membrane of the stethoscope. Filler layers of open cell hard (rigid) foam material, open cell cotton-wool-like soft (flexible) foam material and open cell foam material fill spaces between the discs.

Advantageously the wall of the hollow body has an air exit hole for the emergence of any residual air.

DESCRIPTION OF THE PREFERRED EMBODIMENTS

The invention will hereinafter be further described with reference to the accompanying drawing which is a cross-section through one embodiment of an attachment in accordance with the invention shown attached to the flared end of a wind operated instrument.

The hollow body 1 is of cylindrical shape and has a circular aperture 10, the edge of which is provided with a foam rubber rim 11.

The hollow body 1 is attached to the wind instrument with the round aperture 11 disposed coaxially with the bell 9 of the instrument. The attachment may be fastenend to the bell by releasable elastically extendible fastening means 8. The fastening means 8 comprise a hook 7 and a helical spring 15 which is respectively hinged to an eye-bolt 16 screwed into a wall 5 of the hollow body. At least two such combinations of hook 7 and spring 15 are provided. The hollow body 1 can thus be fastened by the fastening means to bells 9 of differing sizes.

Arranged in the interior 2 of the hollow body 1, between two open cell felt discs 21 which close off the lower aperture of the hollow body and which are permeable to air are dissimilar filler layers and a third similar felt disc 21 which carries a membrane 20 of a stethoscope. The filler layers consist of open cell rigid polymeric foam material 22, open cell flexible polymeric foam material having a cotton or wool-like character 23 and open cell polymeric foam material 24.

The stethoscope membrane 20 is connected via a short piece of tube 19 to piece of tube 3 which extends through an aperture of a sealing sleeve 18 arranged in a corresponding aperture in the wall 5 of the hollow body. Outside the hollow body, the tube 3 branches at the location 17 into two further pipe portions 12, on which are slipped two tubes 6 of the stethoscope. Fastened to the free end of each tube 6 is an ear piece 14, which is inserted into the external auditory meatus of the instrument player.

The attachment described hereinbefore has, on account of its simple construction, an extremely low production price, a very long useful life, a good adaptability to different sizes of instruments and, above all else, an excellent sound attenuation. The sound attenuation which can be achieved with this attachment is so extensive that other people present in the same room are completely undisturbed by the practicing. Conversely, the people in the same room may give rise to noises by speaking, or by operating radio and television, without disturbing the instrument player, since his external auditory meatuses are closed by the ear pieces and are filled by the sound produced by the instrument.

This attachment thus makes it possible for persons living in a confined space and interested in music to approach the learning of a wind operated instrument.

Having thus described my invention in detail and with the particularity required by the Patent Laws, what is desired protected by Letters Patent is set forth in the following claims.

I claim:

1. An attachment for a musical wind instrument, such as trumpet or the like which has a bell-type end, comprising
   - a hollow body having rigid side walls and two unobstructed open ends, one end adapted to fit within the bell-type end of the trumpet,
   - a stethoscope having membrane means and two earpieces, said membrane means being positioned within the hollow body between the ends of said body, said earpieces being located externally of said body,
   - the internal volume of said body not occupied by said membrane means being filled with air-permeable acoustically damping material.

2. Attachment as claimed in claim 1, in which the hollow body is of cylindrical shape and on which a plurality of fastening means are provided, each fastening means being elastically extensible, being disposed on an outer surface of the hollow body and being provided with a respective hook for the releasable connection of the hollow body to the bell-type end of the wind instrument.

3. An attachment as claimed in claims 1 or 2, in which the hollow body is provided with a sealing rim around the aperture of the hollow body to be adjacent the bell-type end of the wind instrument, the sealing rim comprising an elastomer.

4. An attachment as claimed in claims 1 or 2, in which the aperture of the hollow body adjacent the bell and the lower aperture of the cylindrical hollow body are each closed by a felt disc, said discs being permeable to air and having disposed therebetween a third and similar felt disc which supports the membrane of the stethoscope, and filler layers of open cell polymeric rigid foam material, open cell flexible polymeric foam material and open cell polymeric foam material.

5. An attachment as claimed in claims 1 or 2 further comprising air exit hole in the wall of the hollow body.

6. An attachment for a musical wind operated instrument, such as a trumpet or the like, comprising a hollow cylindrical body having unobstructed open ends and shaped such that an open end thereof may be brought into sealed communication with the bell of the instrument, means for securing the hollow cylindrical body to the bell of said instrument, a first permeable felt disc closing the opening of the hollow body to be adjacent the bell of said instrument, a second permeable felt disc near the opposite opening of the hollow cylindrical body and a third permeable felt disc dividing the hollow cylindrical body into two chambers, a stethoscope having a membrane, said membrane mounted within a first chamber, said first chamber lying between the first and third discs, permeable open cell polymeric foam completely filling said first chamber, permeable open cell rigid polymeric foam adjacent the second felt disc partly filling the other chamber between the second and third felt discs within the hollow cylindrical body, and permeable open cell flexible polymeric foam material completely filling the remainder of the other chamber between the rigid foam and third disc.

* * * * *